(12) United States Patent
Fang et al.

(10) Patent No.: US 11,576,662 B2
(45) Date of Patent: Feb. 14, 2023

(54) POSTERIOR NASAL PACKING WITH INTEGRATED SENSOR AS PATIENT TRACKER

(71) Applicant: Acclarent, Inc., Irvine, CA (US)

(72) Inventors: Itzhak Fang, Irvine, CA (US); Ehsan Shameli, Irvine, CA (US); Jetmir Palushi, Irvine, CA (US); Babak Ebrahimi, Irvine, CA (US); Fatemeh Akbarian, Rancho Palos Verdes, CA (US)

(73) Assignee: Acclarent, Inc., Irvine, CA (US)

(*) Notice: Subject to any disclaimer, the term of this patent is extended or adjusted under 35 U.S.C. 154(b) by 449 days.

(21) Appl. No.: 16/683,312

(22) Filed: Nov. 14, 2019

(65) Prior Publication Data

US 2020/0187924 A1 Jun. 18, 2020

Related U.S. Application Data

(60) Provisional application No. 62/779,517, filed on Dec. 14, 2018.

(51) Int. Cl.
| | | |
|---|---|---|
| *A61B 17/00* | (2006.01) | |
| *A61B 17/12* | (2006.01) | |
| *A61B 34/20* | (2016.01) | |

(52) U.S. Cl.
CPC .... *A61B 17/0057* (2013.01); *A61B 17/12104* (2013.01); *A61B 17/12136* (2013.01); *A61B 17/12159* (2013.01); *A61B 34/20* (2016.02); *A61B 2034/2065* (2016.02); *A61B 2217/005* (2013.01); *A61B 2562/227* (2013.01)

(58) Field of Classification Search
CPC .......... A61B 17/0057; A61B 17/12104; A61B 17/12136; A61B 17/12159; A61B 34/20; A61B 2034/2065; A61B 2217/005; A61B 2562/227; A61B 17/24; A61M 2025/0166; A61M 2210/0681
See application file for complete search history.

(56) References Cited

U.S. PATENT DOCUMENTS

| | | | |
|---|---|---|---|
| 7,720,521 B2 | 5/2010 | Chang et al. | |
| 7,727,186 B2* | 6/2010 | Makower | ................ A61F 11/20 606/196 |
| 9,101,384 B2* | 8/2015 | Makower | .......... A61M 25/0068 |
| 2011/0004057 A1 | 1/2011 | Goldfarb et al. | |

(Continued)

*Primary Examiner* — Julian W Woo
(74) *Attorney, Agent, or Firm* — Frost Brown Todd LLP (57) ABSTRACT

An apparatus includes an occlusion device operable to fit securely in an anatomical passageway within a head of a human. The occlusion device is configured to move unitarily with the head when the occlusion device is installed in the anatomical passageway. The occlusion device is further configured to prevent passage of fluid through the anatomical passageway when the occlusion device is installed in the anatomical passageway. A position sensor is fixedly integrated into the occlusion device. The position sensor generates signals indicating a position of the occlusion device in three-dimensional space, thereby indicating the position of the head in three-dimensional space. A connector communicatively coupled to the position sensor is operable to receive and transmit the signals generated by the position sensor.

19 Claims, 4 Drawing Sheets

(56) References Cited

U.S. PATENT DOCUMENTS

| | | | |
|---|---|---|---|
| 2011/0060214 A1* | 3/2011 | Makower | A61B 5/062 606/108 |
| 2012/0245419 A1 | 9/2012 | Makower et al. | |
| 2013/0245608 A1* | 9/2013 | Muni | A61M 29/02 604/285 |
| 2014/0364725 A1 | 12/2014 | Makower | |
| 2016/0008083 A1 | 1/2016 | Kesten et al. | |
| 2017/0007811 A1* | 1/2017 | Vaccaro | A61B 90/90 |
| 2018/0310886 A1 | 11/2018 | Salazar et al. | |

* cited by examiner

POSTERIOR NASAL PACKING WITH INTEGRATED SENSOR AS PATIENT TRACKER

PRIORITY

This application claims priority to U.S. Provisional Pat. App. No. 62/779,517, entitled "Posterior Nasal Packing with Integrated Sensor as Patient Tracker," filed Dec. 14, 2018, the disclosure of which is incorporated by reference herein in its entirety.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein.

In addition to or in lieu of dilating ostia of sinuses, it may be desirable in some instances to irrigate the sinuses to flush contents from the sinuses. For instance, it may be desirable to provide such irrigation for therapeutic purposes and/or in order to clear a site before and/or after a sinuplasty procedure as described herein. Sinus irrigation may be performed using an irrigation catheter that is positioned within the sinus. The irrigation catheter may have one or more distally positioned openings that are configured to emit fluid (e.g., saline) as the fluid is communicated through the irrigation catheter. While procedures such as sinus irrigation are performed, it may be desirable to prevent the irrigation fluid and/or flushed debris from traveling down the patient's nasopharynx. This may be attempted using suction devices, occluding devices, and/or other kinds of devices. A variety of devices that may be used to prevent such travel are described in U.S. Pub. No. 2012/0245419, entitled "Devices, Systems and Methods for Diagnosing and Treating Sinusitis and Other Disorders of the Ears, Nose and/or Throat," published Sep. 27, 2012, now issued as U.S. Pat. No. 8,905,922 on Dec. 9, 2014, the disclosure of which is incorporated by reference herein.

While an endoscope may be used to provide visualization within an anatomical passageway, it may also be desirable to provide additional visual confirmation of the proper positioning of a dilation catheter or some other instrument before performing an operation with that instrument. This may be done using image-guided surgery (IGS), which is a technique where a computer is used to obtain a real-time correlation of the location of an instrument that has been inserted into a patient's body to a set of preoperatively obtained images (e.g., a CT or MRI scan, 3-D map, etc.) so as to superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot, etc.) showing the real time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

While several systems and methods have been made and used in ENT procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Image Guided Surgery Navigation System

Figure 1:
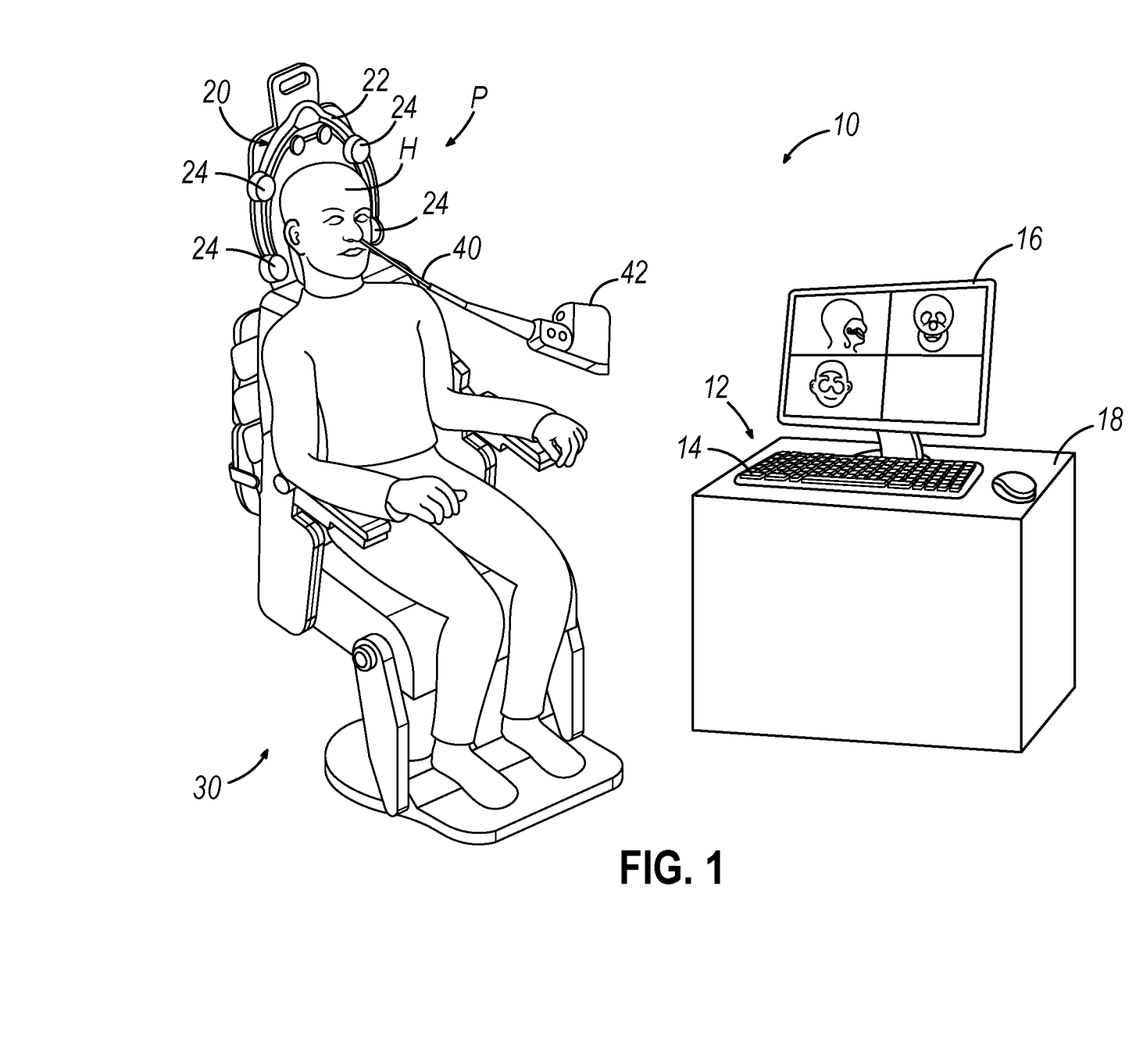
FIG. 1 depicts a schematic view of an exemplary surgery navigation system being used on a patient seated in an exemplary medical procedure chair.

When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). FIG. 1 shows an exemplary IGS navigation system (10) enabling an ENT procedure to be performed using image guidance. In addition to or in lieu of having the components and operability described herein IGS navigation system (10) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

IGS navigation system (10) of the present example comprises a field generator assembly (20), which comprises set of magnetic field generators (24) that are integrated into a horseshoe-shaped frame (22). Field generators (24) are operable to generate alternating magnetic fields of different frequencies around the head (H) of the patient (P). A navigation guidewire (40) is inserted into the head (H) of the patient (P) in this example. Navigation guidewire (40) may be a standalone device or may be positioned on an end effector or other location of a medical instrument such as a surgical cutting instrument or dilation instrument. In the present example, frame (22) is mounted to a chair (30), with the patient (P) being seated in the chair (30) such that frame (22) is located adjacent to the head (H) of the patient (P). By way of example only, chair (30) and/or field generator assembly (20) may be configured and operable in accordance with at least some of the teachings of U.S. Pub. No. 2018/0310886, entitled "Apparatus to Secure Field Generating Device to Chair," published Nov. 1, 2018, now issued as U.S. Pat. No. 10,561,370 on Feb. 18, 2020, the disclosure of which is incorporated by reference herein.

IGS navigation system (10) of the present example further comprises a processor (12), which controls field generators (24) and other elements of IGS navigation system (10). For instance, processor (12) is operable to drive field generators (24) to generate alternating electromagnetic fields; and process signals from navigation guidewire (40) to determine the location of a position sensor in navigation guidewire (40) within the head (H) of the patient (P). Processor (12) comprises a processing unit communicating with one or more memories. Processor (12) of the present example is mounted in a console (18), which comprises operating controls (14) that include a keypad and/or a pointing device such as a mouse or trackball. A physician uses operating controls (14) to interact with processor (12) while performing the surgical procedure.

Navigation guidewire (40) includes a position sensor (not shown) that is responsive to positioning within the alternating magnetic fields generated by field generators (24). A coupling unit (42) is secured to the proximal end of navigation guidewire (40) and is configured to provide communication of data and other signals between console (18) and navigation guidewire (40). Coupling unit (42) may provide wired or wireless communication of data and other signals.

In the present example, the position sensor of navigation guidewire (40) comprises at least one coil at the distal end of navigation guidewire (40). When such a coil is positioned within an alternating electromagnetic field generated by field generators (24), the alternating magnetic field may generate electrical current in the coil, and this electrical current may be communicated along the electrical conduit(s) in navigation guidewire (40) and further to processor (12) via coupling unit (42). This phenomenon may enable IGS navigation system (10) to determine the location of the distal end of navigation guidewire (40) or other medical instrument (e.g., dilation instrument, surgical cutting instrument, etc.) within a three-dimensional space (i.e., within the head (H) of the patient (P), etc.). To accomplish this, processor (12) executes an algorithm to calculate location coordinates of the distal end of navigation guidewire (40) from the position related signals of the coil(s) in navigation guidewire (40). While the position sensor is located in guidewire (40) in this example, such a position sensor may be integrated into various other kinds of instruments, including those described in greater detail below.

Processor (12) uses software stored in a memory of processor (12) to calibrate and operate IGS navigation system (10). Such operation includes driving field generators (24), processing data from navigation guidewire (40), processing data from operating controls (14), and driving display screen (16). In some implementations, operation may also include monitoring and enforcement of one or more safety features or functions of IGS navigation system (10). Processor (12) is further operable to provide video in real time via display screen (16), showing the position of the distal end of navigation guidewire (40) in relation to a video camera image of the patient's head (H), a CT scan image of the patient's head (H), and/or a computer-generated three-dimensional model of the anatomy within and adjacent to the patient's nasal cavity. Display screen (16) may display such images simultaneously and/or superimposed on each other during the surgical procedure. Such displayed images may also include graphical representations of instruments that are inserted in the patient's head (H), such as navigation guidewire (40), such that the operator may view the virtual rendering of the instrument at its actual location in real time. By way of example only, display screen (16) may provide images in accordance with at least some of the teachings of U.S. Pub. No. 2016/0008083, entitled "Guidewire Navigation for Sinuplasty," published Jan. 14, 2016, now issued as U.S. Pat. No. 10,463,242 on Nov. 5, 2019, the disclosure of which is incorporated by reference herein. In the event that the operator is also using an endoscope, the endoscopic image may also be provided on display screen (16).

The images provided through display screen (16) may help guide the operator in maneuvering and otherwise manipulating instruments within the patient's head (H) when such instruments incorporate navigation guidewire (40). It should also be understood that other components of a surgical instrument and other kinds of surgical instruments, as described below, may incorporate a position sensor like the position sensor of navigation guidewire (40).

II. Exemplary Patient Tracker System

In the example described above, where field generators (24) are mounted to frame (22), which is thereby assembled to chair (30), rather than being directly attached to a patient's head (H), the frame of reference for IGS navigation system (10) (i.e., the electromagnetic field generated by field generators (24)) does not move with the head (H) of the patient (P). In some instances, a procedure may involve intentional or inadvertent movements by the patient (P) while situated in chair (30), such that the patient's head (H) may shift positions, location, and/or orientation in relation to support assembly (20). When a navigation guidewire (40) (or other instrument having a position sensor compatible with IGS navigation system (10)) is disposed in the head (H) of the patient (P), IGS navigation system (10) may not be able to differentiate between (i) movement of navigation guidewire (40) relative to the head (H) of the patient (P) and (ii) movement of the head (H) of the patient (P) with navigation guidewire (40) (e.g., when navigation guidewire (40) remains stationary relative to the head (H) of the patient (P) yet moves relative to the electromagnetic field generated by field generators (24)).

Thus, by not securing field generators (24) relative to the head (H) of the patient (P), IGS navigation system (10) may provide inaccurate position data relative to the head (H) of the patient (P) when the head (H) of the patient (P) moves while navigation guidewire (40) is disposed in the head (H) of the patient (P). It may therefore be desirable for IGS navigation system (10) to include features and functionality to account for movement of the patient's head (H), to preserve the accuracy of IGS navigation system (10). Even locating a position sensor on the patient's head (H) may leave room for error, as such a position sensor may be inadvertently moved if the sensor cable is pulled when the patient's head (H) is moved. The placement and removal of an adhesive-secured position sensor on the head (H) of the patient (P) may also be unpleasant for the patient (P).

As an alternative to a position sensor being mounted externally to the head (H) of the patient (P), it may beneficial to fixedly secure a position sensor inside of the head (H) of the patient (P) to thereby enable IGS navigation system (10) to track movement of the head (H) of the patient (P). By fixedly securing the position sensor inside of the head (H), it may reduce the risk of the position sensor becoming inadvertently removed from the head (H) of the patient. Moreover, such a position sensor may be integrated directly into an instrument that would be fixedly secured inside the head (H) of the patient (P) anyway, such that additional instrumentation is not necessary in order to fixedly secure the position sensor inside the head (H) of the patient (P). Integrating a position sensor into an instrument that would be fixedly secured inside the head (H) of the patient (P) anyway may also minimize the obtrusiveness of securing the position sensor inside the head (H) of the patient (P).

The following description provides various examples of a navigation system component that is configured to cooperatively communicate with IGS navigation system (10) to improve accuracy in tracking the position of an instrument (e.g., navigation guidewire (40)) that is inserted into the patient's head. In particular, the navigation system component is configured to be responsive to movement of a patient's head (H) in relation to the fields generated by field generators (24), such that the signals generated by a navigational instrument (e.g., navigation guidewire (40)) may be processed by processor (12) through an error correction algorithm, to effectively subtract-out movement of the head (H) of the patient (P), to thereby accurately determine the three-dimensional location of the navigational instrument within the head (H) of the patient (P).

It should be understood that the navigation system components described below may be readily incorporated into any of the various navigation systems (10) described above and in any of the various medical procedures described in the various references described herein. Other suitable ways in which the below-described navigation system components may be used will be apparent to those of ordinary skill in the art in view of the teachings herein.

III. Exemplary Posterior Nasal Pack with Integral Head Position Sensor

As noted above, it may be desirable in some instances to irrigate the paranasal sinus cavities to flush contents from the paranasal sinus cavities. The process of irrigating the paranasal sinus cavities may be performed using an irrigation catheter or using some other irrigation device. It should be understood that an irrigation process using irrigation catheter may result in the need for fluid and/or other debris to drain from the irrigation/flush site. In addition to irrigation fluid drainage, or even in the absence of irrigation fluid drainage, some procedures (e.g., nasal polyp removal, turbinate reduction, other FESS procedures, etc.) may also result in blood drainage. It may be desirable to prevent such irrigation fluid, blood, and/or other fluids from draining down the patient's throat. Otherwise, the patient may gag, cough, choke, or otherwise experience discomfort. In some instances, the operator may simply have the patient lean forward such that the fluid drains from the patient's nose or mouth. As an alternative to this approach, an occlusion device may be positioned within the patient's head, such as the nasopharynx, in the posterior choana, or elsewhere to prevent the fluid from draining down the patient's throat. In addition or in the alternative, a suction device may be used to draw away the fluid drainage. Additional devices that may be used to handle drainage from an irrigation process will be described in greater detail below; while still other examples will be apparent to those of ordinary skill in the art in view of the teachings herein.

Figure 2:
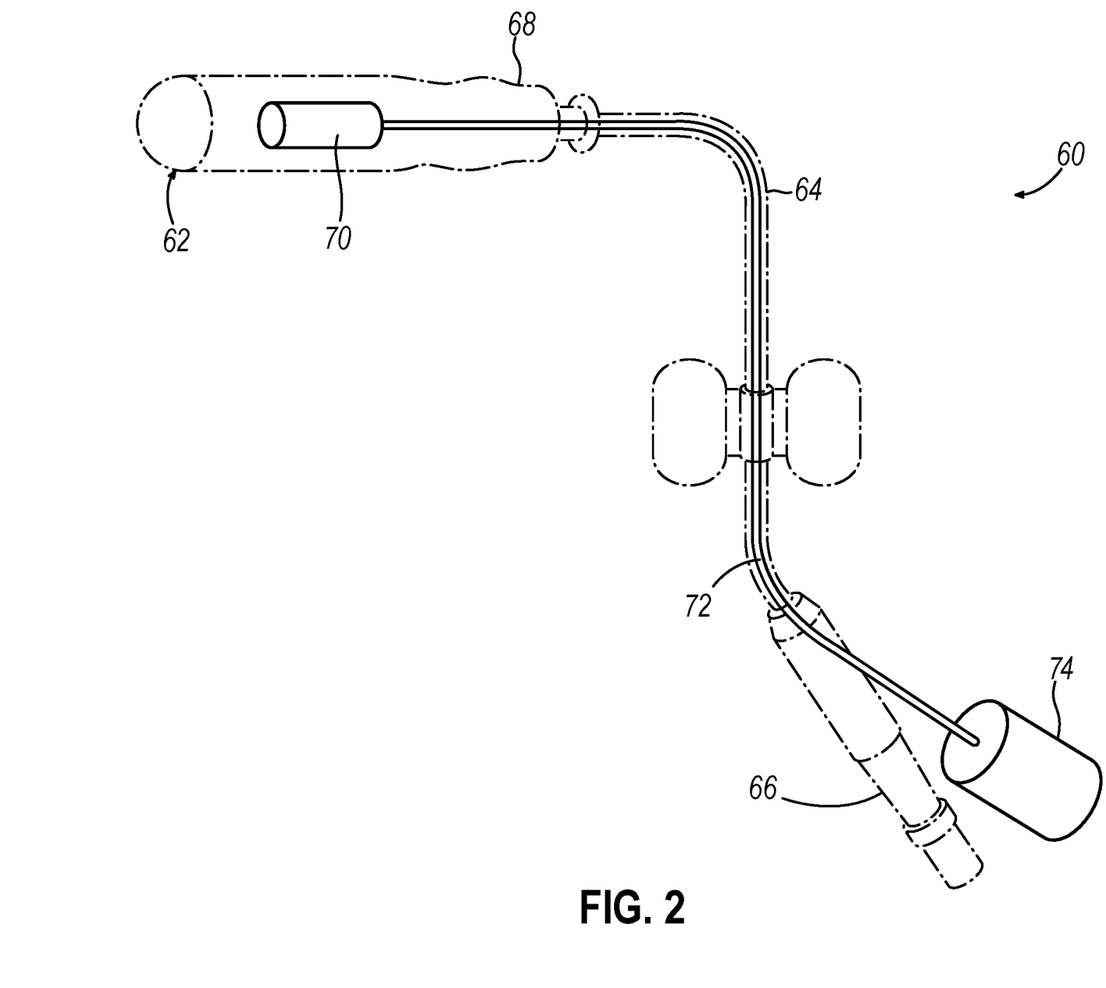
FIG. 2 depicts a perspective view of an exemplary posterior nasal pack with integrated sensor.

FIG. 2 shows an exemplary posterior nasal pack (60) that may be used to handle drainage from an irrigation procedure performed using irrigation catheter or using some other irrigation device; or some other procedure that creates some kind of fluid drainage. Nasal pack (60) of this example comprises an absorbent member (68) secured around a body (62). Body (62) may comprise a balloon or other kind of body that enables absorbent member (68) and body (62) to be fixedly positioned within the posterior choana or the nasopharynx of a patient. The distal end of a catheter tube (64) is secured to body (62) with a fluid tight seal at the interface between catheter tube (64) and body (62).

The proximal end of catheter tube (64) includes a port (66). In versions where body (62) comprises a balloon, body (62) is in fluid communication with catheter tube (64). Port (66) may be coupled with an inflation fluid source (e.g., saline-filled syringe, etc.) to thereby selectively inflate the balloon. In some other versions (e.g., versions where body (62) lacks a balloon), absorbent member (68) is in fluid communication with catheter tube (64). In such versions, port (66) may be coupled with a suction source (e.g., vacuum pump, vacuum wall outlet, syringe, etc.), such that catheter tube (64) may provide suction from the suction source to absorbent member (68) and thereby draw excess fluids from absorbent member (68). As yet another merely illustrative variation, the proximal end of catheter tube (64) may include two ports—one for providing the inflation described above and the other for providing the suction described above.

Body (68) is configured to absorb fluids and is also pliable such that body (68) does not cause trauma to the tissue that comes in contact with body (68). In some versions, body (68) is configured to expand as it absorbs fluid, such that body (68) will at least slightly bear outwardly on the inner wall of the anatomical passageway in which body (68) is disposed. This may enable body (68) to generally conform to the shape of the anatomical passageway and avoid fluids leaking past body (68). In some versions, body (68) comprises foam, or alternatively or additionally, a sterile tampon. Various suitable materials and structures that may be used to form body (68) will be apparent to those of ordinary skill in the art in view of the teachings herein. In some versions, body (68) may not be present or may be removable prior to insertion of body (62) into the anatomical passageway. An application of one or more anesthetics, coagulants, or other medications may be applied to body (68) prior to insertion.

Body (62) is also pliable and atraumatic, yet body (62) is formed of a non-absorbent material that will provide a fluid tight seal such that the fluid will not pass through or around body (62) when body (62) is properly positioned within an anatomical passageway such as the posterior choana or the nasopharynx. In some versions, body (62) comprises a membrane. Body (62) may also resiliently bear against the wall of the anatomical passageway, such that body (62) conforms to the shape of the anatomical passageway without providing fluid drainage paths between the outer perimeter of body (62) and the wall of the anatomical passageway. It should be understood that body (68) and body (62) may have any suitable relative thicknesses. Various suitable materials that may be used to form body (62) will also be apparent to those of ordinary skill in the art in view of the teachings herein.

In an exemplary use, posterior nasal pack (60) is positioned in a patient's posterior choana or nasopharynx while an irrigation catheter is positioned at the irrigation site in the patient's nasal cavity. In this example, catheter tube (64) exits the head (H) of the patient (P) via the patient's mouth or nostril. Irrigation fluid is then communicated through the irrigation catheter while suction is communicated to catheter tube (64). The irrigation fluid drains through the patient's nasal cavity and into body (68), which absorbs the fluid. As body (68) absorbs the fluid, catheter tube (64) draws the fluid out of body (68) via the suction source that is coupled with suction port (66). This prevents body (68) from becoming oversaturated to the point where posterior nasal pack (60) no longer effectively plugs the drainage path. The configuration and absorbance of body (68) prevents fluid from flowing quickly past catheter tube (64).

During normal use, body (68) does not move within the head (H) of the patient (P) as the irrigation procedure and other medical procedures are conducted within the head (H) of the patient (P). Thus, once posterior nasal pack (60) is installed in the head (H) of the patient (P), the position of posterior nasal pack (60) will not move relative to the head (H) of the patient (P) until the operator intentionally removes posterior nasal pack (60) at the end of the procedure.

As also shown in FIG. 2, posterior nasal pack (60) further includes a head position sensor (70), which is in communication with proximal IGS system connector (74) through a communication wire (72). In the present example, head position sensor (70) is fixedly secured in body (62), though head position sensor (70) may instead be fixedly secured to any other portion of posterior nasal pack (60) that that moves unitarily with the head (H) of the patient (P) during the medical procedure. IGS system connector (74) is configured to couple with processor (12) of IGS navigation system (10). In some versions, proximal IGS system connector (74) or some other component that is coupled with communication wire (72) includes an EEPROM or other storage device that is configured to store calibration data associated with calibration of head position sensor (70) relative to IGS navigation system (10). Other suitable components that IGS system connector (74) may incorporate, and various suitable forms that IGS system connector (74) may take, will be apparent to those skilled in the art in view of the teachings herein.

The inclusion of head position sensor (70) in posterior nasal pack (60) thus provides compatibility with IGS navigation system (10). Posterior nasal pack (60) fixedly houses head position sensor (70) so the position of the patient's head (H) can be tracked while posterior nasal pack (60) is inside of the patient's head (H). Since the posterior nasal pack (60) is secured inside of the head (H) of the patient (P), head position sensor (70) can track the movements of the head (H) of the patient (P) accurately. Moreover, by being fixedly integrated into posterior nasal pack (60), which is fixedly secured within the head (H) of the patient (P), it may be relatively unlikely that position sensor (70) inadvertently moves within the head (H) of the patient (P).

Head position sensor (70) of the present example comprises at least one wire coil wrapped about at least one respective axis. One or more communication wires (72) may extend through or along catheter tube (64) from head position sensor (70) to proximal IGS system connector (74) to thereby provide a path for communication of position-indicative signals from head position sensor (70) to proximal IGS system connector (74). Proximal IGS system connector (74) may be further coupled with processor (12) of IGS navigation system (10) in any suitable fashion (e.g., similar to coupling unit (42) described above), thereby enabling position-indicative signals from head position sensor (70) to reach processor (12). When head position sensor (70) is positioned within an alternating electromagnetic field generated by field generators (24), the alternating magnetic field may generate electrical current in head position sensor (70), and this electrical current may be communicated along the wire(s) (72) to proximal IGS system connector (74) and further to processor (12). This phenomenon may enable IGS navigation system (10) to determine the location of head position sensor (70) within a three-dimensional space (i.e., within the head (H) of the patient (P), etc.). To accomplish this, processor (12) executes an algorithm to calculate location coordinates of the head position sensor (70) from the position related signals of head position sensor (70), which in turn provides the location of the head (H).

It should be understood from the foregoing that, as the head (H) of a patient (P) is moved while the head position sensor (70) is inside the head (H), real-time feedback of the movement will be received. Signals generated by movement of head position sensor (70) may allow processor (12) to determine the three-dimensional location and orientation of head (H) of patient (P) relative to the plurality of field generators (24). Processor (12) may utilize this information, in conjunction with the location of navigation guidewire (40) (or any other suitable instrument that has an integral position sensor) relative to field generators (24), to subtract out movement of the head (H) of the patient (P) from movement of navigation guidewire (40) (or any other suitable instrument that has an integral position sensor). Processor (12) may then drive display screen (16) to accurately display the location of navigation guidewire (40) (or any other suitable instrument that has an integral position sensor) within head (H) of the patient (P) despite movement of the head (H) of the patient (P).

IV. Exemplary Foley Catheter with Integral Head Position Sensor

Figure 3:
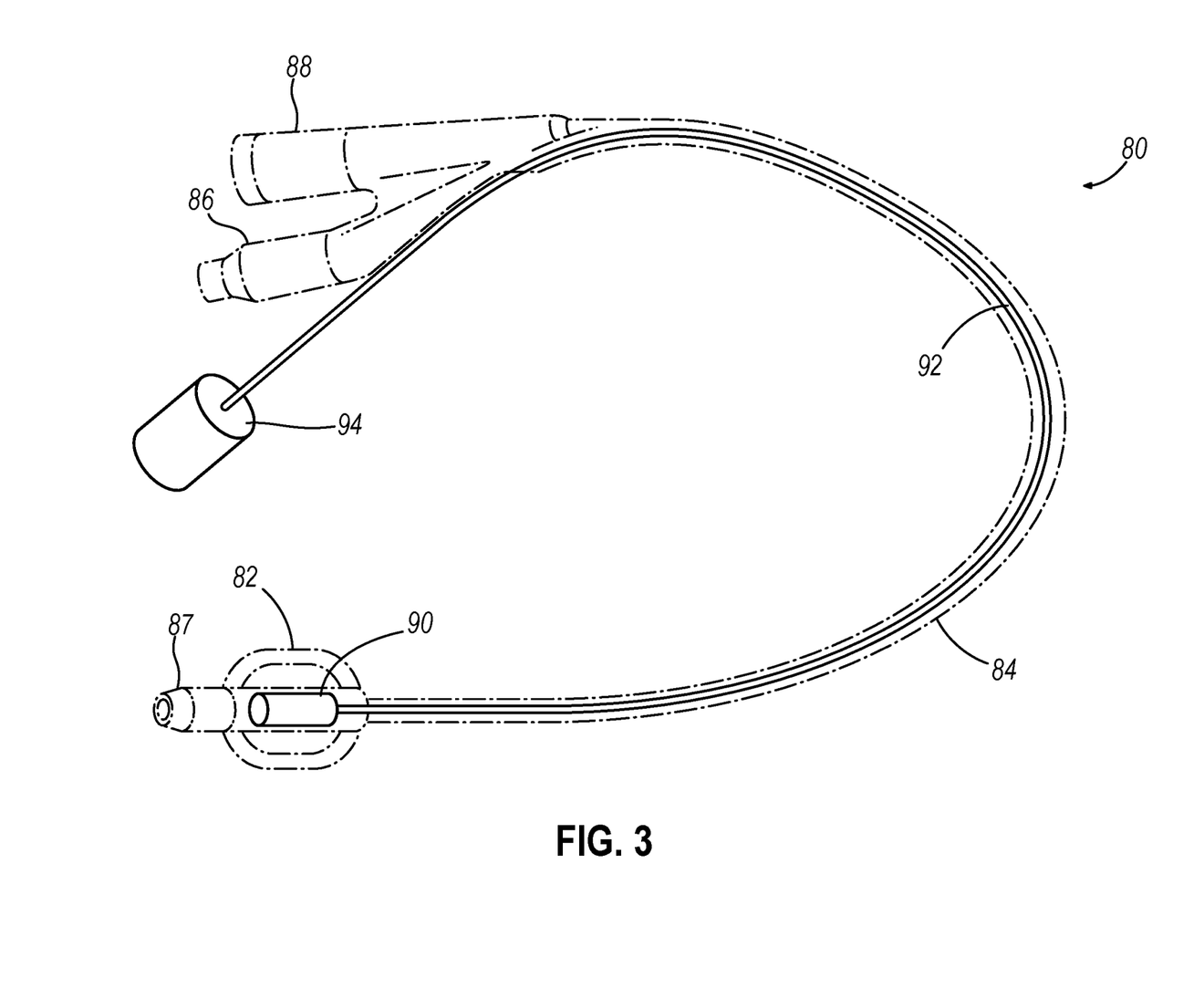
FIG. 3 depicts a perspective view of an exemplary Foley catheter with integrated positioning sensor.
Figure 4:
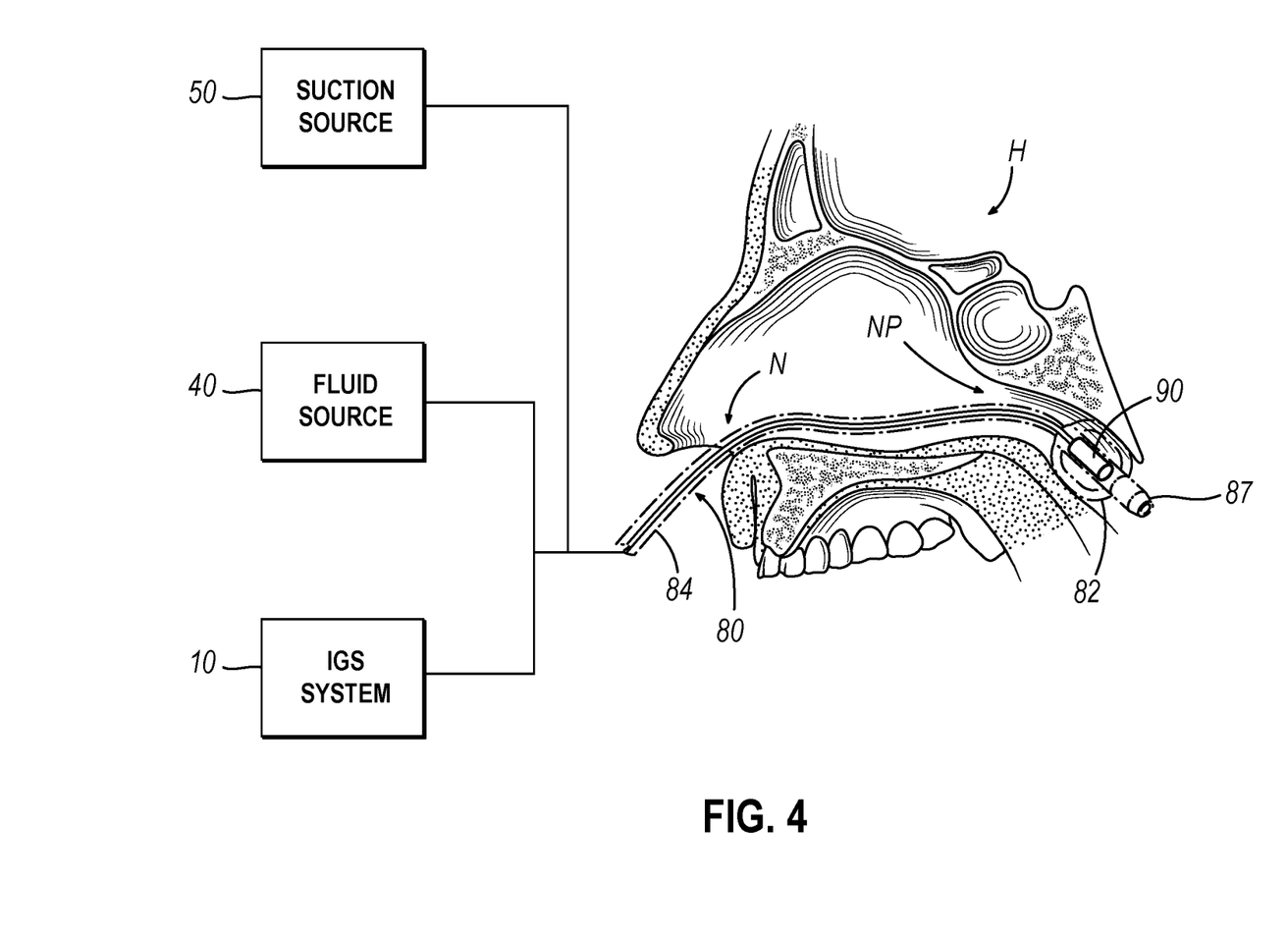
FIG. 4 depicts a diagrammatic view of the Foley catheter of FIG. 3 positioned within a nasopharynx of a patient.

FIGS. 3-4 show an exemplary Foley catheter (80) that may be used to handle drainage from an irrigation procedure performed using irrigation catheter or using some other irrigation device; or some other procedure that creates some kind of fluid drainage. Foley catheter (80) of this example comprises a balloon (82) and a catheter tube (84). A suction nozzle (87) is positioned distal to balloon (82) and is operable to communicate suction via one or more openings to the environment in which suction nozzle (87) is positioned. In some versions, catheter tube (84) further includes one or more suction openings that are proximal to balloon (82). Catheter tube (84) is secured to balloon (82) with a fluid tight seal at the interface between catheter tube (84) and balloon (82).

The proximal end of catheter tube (84) includes a suction port (86) and an inflation port (88). Catheter tube (84) further defines two discrete lumens—one in fluid communication with suction port (86) (and any suction openings that are proximal to balloon (82), if applicable); and another in fluid communication with inflation port (88). The suction lumen is further in fluid communication with suction nozzle (87), such that the suction lumen provides a fluid pathway between suction port (86) and suction nozzle (87) (and any suction openings that are proximal to balloon (82), if applicable). The inflation lumen is further in fluid communication with balloon (82), such that the inflation lumen provides a fluid pathway between inflation port (88) and balloon (82). Suction port (86) may be coupled with any suitable suction source (50) (e.g., vacuum pump, vacuum wall outlet, syringe, etc.), as shown in FIG. 4. Similarly, inflation port (88) may be coupled with any suitable inflation fluid source (40) (e.g., a saline-filled syringe, etc.), as shown in FIG. 4.

Balloon (82) is configured to expand within an anatomical passageway such as the posterior choana or the nasopharynx to thereby create a barrier preventing fluid from passing between the sidewall of balloon (82) and the sidewall of the anatomical passageway. Balloon (82) is also pliable and atraumatic, yet balloon (82) is formed of a non-absorbent material that will provide a fluid tight seal such that the fluid will not pass through or around balloon (82) when balloon (82) is properly positioned and inflated within an anatomical passageway such as the posterior choana or the nasopharynx. Balloon (82) may also resiliently bear against the wall of the anatomical passageway, such that balloon (82) conforms to the shape of the anatomical passageway without providing fluid drainage paths between the outer perimeter of balloon (82) and the wall of the anatomical passageway. Various suitable materials that may be used to form balloon (82) will be apparent to those of ordinary skill in the art in view of the teachings herein.

In an exemplary use, as shown in FIG. 4, Foley catheter (80) is positioned in a patient's posterior choana or nasopharynx (NP) via the patient's nostril (N). In some cases, the patient (P) will be sedated during the process describe herein. While catheter tube (84) exits the head (H) of the patient (P) via the patient's nostril (N) in this example, catheter tube (84) may instead exit the head (H) of the patient (P) via the patient's mouth. In versions where catheter tube (84) exits the head (H) of the patient (P) via the patient's nostril (N), it may be preferable to include one or more suction openings in catheter tube (84) just proximal to balloon (82). In versions where catheter tube (84) exits the head (H) of the patient (P) via the patient's mouth, the presence of suction nozzle (87) alone may suffice for suction purposes, such that additional suction openings in catheter tube (84) just proximal to balloon (82) are not necessarily required.

Once Foley catheter (80) is suitably positioned such that balloon (82) is properly positioned in the nasopharynx (NP), fluid source (40) may be activated to inflate balloon (82) to thereby effectively seal the nasopharynx (NP). The position of balloon (82) will be substantially fixed in the head (H) of the patient (P) at this point. The operator may then commence the medical procedure, which may include using other instruments to perform sinuplasty, polyp removal, turbinate reduction, and/or any other procedures as may be desired within or adjacent to the nasal cavity. As part of such procedures, irrigation fluid, blood, medication, and/or other fluids may be present in the nasal cavity, in need of drainage. The operator may apply suction via suction source (50) to draw away such fluids via suction nozzle (87) and/or any openings in catheter tube (84) proximal to balloon (82); while inflated balloon (82) further prevents such fluids from draining down the patient's throat.

At the end of the medical procedure, balloon (82) may be deflated. Foley catheter (80) may then be pulled out of the head (H) of the patient (P) via the patient's nostril (or via the patient's mouth in cases where catheter tube (84) was passed through the patient's mouth). While FIG. 4 shows Foley catheter (80) installed in the head (H) of the patient (P), posterior nasal pack (60) may be used in a similar fashion, with body (62) and absorbent member (68) being positioned in the nasopharynx (NP). Moreover, posterior nasal pack (60) may be positioned such that catheter tube (64) exits the head (H) of the patient (P) either via the patient's nostril (N) or via the patient's mouth.

During normal use, balloon (82) does not move within the head (H) of the patient (P) as the irrigation procedure and other medical procedures are conducted within the head (H) of the patient (P). Thus, once Foley catheter (80) is installed in the head (H) of the patient (P), the position of Foley catheter (80) will not move relative to the head (H) of the patient (P) until the operator intentionally removes Foley catheter (80) at the end of the procedure.

As also shown in FIG. 3, Foley catheter (80) further includes a head position sensor (90), which is in communication with proximal IGS system connector (94) through a communication wire (92). In the present example, head position sensor (90) is fixedly secured in balloon (82), though head position sensor (90) may instead be fixedly secured to any other portion of Foley catheter (80) that that moves unitarily with the head (H) of the patient (P) during the medical procedure. IGS system connector (94) is configured to couple with processor (12) of IGS navigation system (10), as shown in FIG. 4. In some versions, proximal IGS system connector (94) or some other component that is coupled with communication wire (92) includes an EEPROM or other storage device that is configured to store calibration data associated with calibration of head position sensor (90) relative to IGS navigation system (10). Other suitable components that IGS system connector (94) may incorporate, and various suitable forms that IGS system connector (94) may take, will be apparent to those skilled in the art in view of the teachings herein.

The inclusion of the head position sensor (90) in Foley catheter (80) thus provides compatibility with IGS navigation system (10). Foley catheter (80) fixedly houses head position sensor (90) so the position of the patient's head (H) can be tracked while Foley catheter (80) is inside of the patient's head (H). Since the Foley catheter (80) is secured inside of the head (H) of the patient (P), head position sensor (90) can track the movements of the head (H) of the patient (P) accurately. Moreover, by being fixedly integrated into Foley catheter (80), which is fixedly secured within the head (H) of the patient (P), it may be relatively unlikely that position sensor (90) inadvertently moves within the head (H) of the patient (P).

Head position sensor (90) of the present example comprises at least one wire coil wrapped about at least one respective axis. One or more communication wires (92) may extend through or along catheter tube (84) from head position sensor (90) to proximal IGS system connector (94) to thereby provide a path for communication of position-indicative signals from head position sensor (90) to proximal IGS system connector (94). Proximal IGS system connector (94) may be further coupled with processor (12) of IGS navigation system (10) in any suitable fashion (e.g., similar to coupling unit (42) described above), thereby enabling position-indicative signals from head position sensor (90) to reach processor (12). When head position sensor (90) is positioned within an alternating electromagnetic field generated by field generators (24), the alternating magnetic field may generate electrical current in head position sensor (90), and this electrical current may be communicated along the wire(s) (92) to proximal IGS system connector (94) and further to processor (12). This phenomenon may enable IGS navigation system (10) to determine the location of head position sensor (90) within a three-dimensional space (i.e., within the head (H) of the patient (P), etc.). To accomplish this, processor (12) executes an algorithm to calculate location coordinates of the head position sensor (90) from the position related signals of head position sensor (90), which in turn provides the location of the head (H).

It should be understood from the foregoing that, as the head (H) of a patient (P) is moved while the head position sensor (90) is inside the head (H), real-time feedback of the movement will be received. Signals generated by movement of head position sensor (90) may allow processor (12) to determine the three-dimensional location and orientation of head (H) of patient (P) relative to the plurality of field generators (24). Processor (12) may utilize this information, in conjunction with the location of navigation guidewire (40) (or any other suitable instrument that has an integral position sensor) relative to field generators (24), to subtract out movement of the head (H) of the patient (P) from movement of navigation guidewire (40) (or any other suitable instrument that has an integral position sensor). Processor (12) may then drive display screen (16) to accurately display the location of navigation guidewire (40) (or any other suitable instrument that has an integral position sensor) within head (H) of the patient (P) despite movement of the head (H) of the patient (P).

While the examples described above provide position of body (62) and balloon (82) in the nasopharynx (NP) or choana, other variations may provide positioning of body (62) or balloon (82) (or variations of body (62) or balloon (82)) in other locations within the patient (P). Other suitable locations for positioning of such elements will be apparent to those skilled in the art in view of the teachings herein. Moreover, other variations may provide integration of a position sensor (70, 90) into some other device that will otherwise be fixedly secured relative to the patient (P) such that the integrated position sensor (70, 90) will move unitarily with the head (H) of the patient (P). By way of example only, some medical procedures may warrant use of an endotracheal intubation assembly. In such cases, a position sensor (70, 90) may be integrated into the endotracheal intubation assembly since the endotracheal intubation assembly will be installed in the patient (P) anyway, and since the endotracheal intubation assembly will move unitarily with the head (H) of the patient (P). As another merely illustrative example, some medical procedures may warrant the use of a laryngeal mask airway device. In such cases, a position sensor (70, 90) may be integrated into the laryngeal mask airway device since the laryngeal mask airway device will be installed in the patient (P) anyway, and since the laryngeal mask airway device will move unitarily with the head (H) of the patient (P). Various suitable ways in which a position sensor (70, 90) may be integrated into the endotracheal intubation assembly or laryngeal mask airway device will be apparent to those skilled in the art in view of the teachings herein.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus comprising: (a) an occlusion device configured to fit securely in an anatomical passageway within a head of a human, wherein the occlusion device is configured to move unitarily with the head when the occlusion device is installed in the anatomical passageway, wherein the occlusion device is further configured to prevent passage of fluid through the anatomical passageway when the occlusion device is installed in the anatomical passageway; (b) a position sensor fixedly secured on the occlusion device, wherein the position sensor is configured to generate signals indicating a position of the occlusion in three-dimensional space; (c) a conduit extending proximally from the occlusion device, wherein the conduit includes a first lumen in fluid communication with the occlusion device; and (d) a connector communicatively coupled to the position sensor, wherein the connector is configured to receive and transmit the signals generated by the position sensor.

EXAMPLE 2

The apparatus of Example 1, wherein the occlusion device comprises a posterior nasal pack.

EXAMPLE 3

The apparatus of Example 2, wherein the posterior nasal pack comprises an absorbent member.

EXAMPLE 4

The apparatus of Example 3, wherein the posterior nasal pack further comprises a medication is applied to the absorbent member.

EXAMPLE 5

The apparatus of any one or more of Examples 1 through 4, wherein the occlusion device is configured to conform to the shape of the anatomical passageway.

EXAMPLE 6

The apparatus of any one or more of Examples 1 through 5, wherein the conduit further includes a suction port in fluid communication with the first lumen, wherein the suction port is configured to couple with a suction source and thereby provide suction from the suction source to the first lumen.

EXAMPLE 7

The apparatus of Example 6, further comprising at least one suction opening positioned on or near the occlusion device, wherein the at least one suction opening is in fluid communication with the first lumen such that the suction port and the first lumen are operable to communicate suction from the suction source to the at least one suction opening.

EXAMPLE 8

The apparatus of any one or more of Examples 1 through 7, wherein the occlusion device is sized to be positioned within a human nasopharynx or choana.

EXAMPLE 9

The apparatus of any one or more of Examples 1 through 8, wherein the connector is located at a proximal end of the conduit.

EXAMPLE 10

The apparatus of Example 9, wherein the position sensor is in communication with the connector through one or more communication wires.

EXAMPLE 11

The apparatus of Example 10, wherein the one or more communication wires extend through the conduit.

EXAMPLE 12

The apparatus of any one or more of Examples 1 through 11, wherein the position sensor is positioned within the occlusion device.

EXAMPLE 13

The apparatus of any one or more of Examples 1 through 12, wherein the position sensor is positioned on an exterior of the occlusion device.

EXAMPLE 14

The apparatus of any one or more of Examples 1 through 13, wherein the occlusion device comprises an inflatable balloon.

EXAMPLE 15

The apparatus of Example 14, wherein the conduit further includes an inflation port in fluid communication with first lumen, wherein the first lumen is further in fluid communication with the balloon, wherein the inflation port is configured to couple with an inflation fluid source and thereby provide inflation fluid from the inflation fluid source to the balloon.

EXAMPLE 16

The apparatus of Example 15, further comprising at least one suction opening spaced longitudinally from the inflatable balloon, the conduit further including: (i) a second lumen in fluid communication with the at least one suction opening, and (ii) a suction port in fluid communication with the second lumen, wherein the suction port is configured to couple with a suction source and thereby provide suction from the suction source to the at least one suction opening via the second lumen.

EXAMPLE 17

An apparatus comprising: (a) an occlusion assembly comprising: (i) an occlusion device configured to fit securely in an anatomical passageway within a head of a human, and (ii) a position sensor fixedly secured relative to the occlusion device, wherein the position sensor is configured to generate signals indicating a position of the position sensor in three-dimensional space and thereby indicate a position of the head in three-dimensional space; and (b) an image guided surgery system in communication with the position sensor, wherein the image guided surgery system is configured to determine the position of the head in three-dimensional space based on signals from the position sensor.

EXAMPLE 18

The apparatus of any one or more of Example 17, wherein the image guided surgery system is operable to generate an alternating magnetic field, wherein the position sensor is operable to generate the signals indicating a position of the head in three-dimensional space in response to the alternating magnetic field.

EXAMPLE 19

The apparatus of any one or more of Examples 17 through 18, further comprising a cable coupling the image guided surgery system with the occlusion assembly, wherein the cable is configured to communicate signals from the position sensor to the image guided surgery system.

EXAMPLE 20

A method comprising: (a) inserting an occlusion device into a patient's head, wherein the occlusion device fits securely in an anatomical passageway within the head and occludes the anatomical passageway, wherein the occlusion device includes a first position sensor operable to generate signals indicating a position of the head in three-dimensional space in real time; (b) inserting a working instrument in the head, wherein the instrument includes a second position sensor operable to generate signals indicating a position of the second position sensor in three-dimensional space in real time; and (c) observing a display showing the real time position of the working instrument in the head, wherein the display is driven by a processor in communication with the first and second position sensors, wherein the processor factors in position data from the first position sensor and position data from the second sensor to determine the real time position of the working instrument in the head.

VI. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
(a) an occlusion device configured to fit securely in an anatomical passageway within a head of a human, wherein the occlusion device is configured to be stationary within the anatomical passageway and to thereby move unitarily with the head when the occlusion device is installed in the anatomical passageway, wherein the occlusion device comprises an absorbent body and is further configured to prevent passage of fluid through the anatomical passageway past the occlusion device when the occlusion device is installed in the anatomical passageway;
(b) a position sensor fixedly secured within the absorbent body, wherein the position sensor is configured to generate signals indicating a position of the occlusion device in three-dimensional space and thereby indicate a position of the head in three-dimensional space;

(c) a fluid conduit extending proximally from the occlusion device, wherein the fluid conduit includes a distal end and a first lumen in fluid communication with the occlusion device;

(d) an electrically communicative conduit extending through the fluid conduit and distally past the distal end of the fluid conduit and into the occlusion device; and (e) a connector, wherein the electrically communicative conduit is in electrical communication with the position sensor and the connector, wherein the connector is configured to receive and transmit the signals generated by the position sensor.

2. The apparatus of claim 1, wherein the occlusion device comprises a posterior nasal pack.

3. The apparatus of claim 2, wherein the posterior nasal pack further comprises a medication applied to the absorbent body.

4. The apparatus of claim 1, wherein the occlusion device is configured to conform to a shape of the anatomical passageway.

5. The apparatus of claim 1, wherein the fluid conduit further includes a suction port in fluid communication with the first lumen, wherein the suction port is configured to couple with a suction source and thereby provide suction from the suction source to the first lumen.

6. The apparatus of claim 5, further comprising at least one suction opening positioned on or near the occlusion device, wherein the at least one suction opening is in fluid communication with the first lumen such that the suction port and the first lumen are operable to communicate suction from the suction source to the at least one suction opening.

7. The apparatus of claim 1, wherein the occlusion device is sized to be positioned within a human nasopharynx or choana.

8. The apparatus of claim 1, wherein the connector is located at a proximal end of the fluid conduit.

9. The apparatus of claim 8, wherein the electrically communicative conduit comprises a communication wire.

10. The apparatus of claim 9, wherein the communication wire extends proximally beyond the fluid conduit.

11. The apparatus of claim 1, wherein the position sensor comprises a wire coil.

12. The apparatus of claim 1, wherein the position sensor is configured to indicate the position of the head in real-time.

13. The apparatus of claim 1, wherein the occlusion device further comprises an inflatable balloon.

14. The apparatus of claim 13, wherein the fluid conduit further includes an inflation port in fluid communication with first lumen, wherein the first lumen is further in fluid communication with the balloon, wherein the inflation port is configured to couple with an inflation fluid source and thereby provide inflation fluid from the inflation fluid source to the balloon.

15. The apparatus of claim 14, further comprising at least one suction opening spaced longitudinally from the inflatable balloon, the fluid conduit further including:

(i) a second lumen in fluid communication with the at least one suction opening, and (ii) a suction port in fluid communication with the second lumen, wherein the suction port is configured to couple with a suction source and thereby provide suction from the suction source to the at least one suction opening via the second lumen.

16. An apparatus comprising:
(a) an occlusion assembly comprising:
(i) an occlusion device configured to fit securely in an anatomical passageway within a head of a human, the occlusion device comprising:
(A) a conduit,
(B) an inflatable member fixedly secured to the conduit, wherein the conduit is in fluid communication with the inflation member to thereby provide inflation fluid to the inflation member, and
(C) an absorbent member fixedly secured around the inflatable member, and
(ii) a first position sensor fixedly secured relative to the occlusion device, wherein the first position sensor is configured to generate signals indicating a position of the first position sensor in three-dimensional space and thereby indicate a real-time position of the head in three-dimensional space and move with the head to thereby provide tracking of movement of the head in real time;
(b) a working instrument configured to move within the head of the human, the working instrument including a second position sensor, wherein the second position sensor is configured to generate signals indicating a position of the second position sensor in three-dimensional space and thereby indicate a position of the working instrument in three-dimensional space; and
(c) an image guided surgery system in communication with the first position sensor and the second position sensor, wherein the image guided surgery system is configured to:
(i) determine the real-time position of the head in three-dimensional space based on signals from the first position sensor,
(ii) determine the real-time position of the working instrument in three-dimensional space based on signals from the second position sensor, and
(iii) determine the real-time position of the working instrument relative to the head based on the determined real-time position of the head in three-dimensional space and the determined real-time position of the working instrument in three-dimensional space.

17. The apparatus of claim 16, wherein the image guided surgery system is operable to generate an alternating magnetic field, wherein the position sensor is operable to generate the signals indicating a position of the head in three-dimensional space in response to the alternating magnetic field.

18. The apparatus of claim 16, further comprising a cable coupling the image guided surgery system with the occlusion assembly, wherein the cable is configured to communicate signals from the position sensor to the image guided surgery system.

19. A method comprising:
(a) inserting an occlusion device into a patient's head, wherein the occlusion device moves with the head by fitting securely in an anatomical passageway within the head and occludes the anatomical passageway, wherein the occlusion device includes a first position sensor generating signals indicating a position of the head in three-dimensional space in real time and thereby providing real-time tracking of movement of the head;
(b) inserting a working instrument in the head, wherein the instrument includes a second position sensor operable to generate signals indicating a position of the second position sensor in three-dimensional space in real time;

(c) observing a display showing the real time position of the working instrument in the head, wherein the display is driven by a processor in communication with the first and second position sensors, wherein the processor factors in position data from the first position sensor and position data from the second sensor to determine the real time position of the working instrument in the head, and (d) absorbing occluded fluid using the occlusion device.

\* \* \* \* \*